(12) United States Patent
Serra et al.

(10) Patent No.: US 12,171,420 B2
(45) Date of Patent: Dec. 24, 2024

(54) SURGICAL RETRACTION SYSTEM

(71) Applicant: NuVasive, Inc., San Diego, CA (US)

(72) Inventors: Michael Serra, San Diego, CA (US); Samuel Tome, San Diego, CA (US); Byron Riemhofer, San Diego, CA (US); Shane Fedon, Elfin Forest, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/589,369

(22) Filed: Jan. 31, 2022

(65) Prior Publication Data

US 2023/0240671 A1 Aug. 3, 2023

(51) Int. Cl.
*A61B 17/02* (2006.01)
*A61B 17/00* (2006.01)

(52) U.S. Cl.
CPC .. *A61B 17/0206* (2013.01); *A61B 2017/0042* (2013.01); *A61B 2017/00486* (2013.01)

(58) Field of Classification Search
CPC ............ A61B 2017/0256; A61B 17/025
See application file for complete search history.

(56) References Cited

U.S. PATENT DOCUMENTS

| | | | |
|---|---|---|---|
| 6,464,634 B1* | 10/2002 | Fraser | A61B 17/0293 600/233 |
| 2006/0264946 A1* | 11/2006 | Young | A61B 17/8052 606/915 |
| 2018/0168566 A1* | 6/2018 | O'Connell | A61B 90/57 |
| 2018/0206833 A1 | 7/2018 | O'Connell et al. | |
| 2019/0216453 A1* | 7/2019 | Predick | A61B 17/0206 |
| 2020/0093529 A1* | 3/2020 | Biedermann | A61B 17/0218 |
| 2022/0175362 A1* | 6/2022 | Considine | A61B 17/0206 |

OTHER PUBLICATIONS

Mobbs, R.J. et al., "Lumbar interbody fusion: techniques, indications and comparison of interbody fusion options including PLIF, TLIF, MI-TLIF, OLIF/ATP, LLIF and ALIF," Journal of Spine Surgery, Dec. 2015, 7 pages.

* cited by examiner

*Primary Examiner* — Julianna N Harvey
*Assistant Examiner* — Angel Roberto Mora-Velazquez

(57) ABSTRACT

An example retraction system includes a first retraction assembly, the first retraction assembly including a first arm coupled to a rack, a second arm coupled to the rack, a first retractor blade coupled to the first arm and a second retractor blade coupled to the second arm. The retraction system also includes a second retraction assembly, the second retraction assembly including a carriage configured to engage a blade post having a blade coupled to a distal end and a handle coupled to a proximal end, the blade post adjustable relative to the carriage. The retraction system also includes a third retractor blade coupled to the blade post.

14 Claims, 12 Drawing Sheets

SURGICAL RETRACTION SYSTEM

BACKGROUND

There are a wide variety of surgical medical devices. Some of these devices include surgical retractors, surgical retractor systems, and the like. Of the known surgical medical devices, each has certain advantages and disadvantages. There is an ongoing need to provide alternative surgical medical devices.

BRIEF SUMMARY

This disclosure provides design, material, manufacturing method, and use alternatives for medical devices. An example retraction system includes a first retraction assembly, the first retraction assembly including a first arm coupled to a rack, a second arm coupled to the rack, a first retractor blade coupled to the first arm and a second retractor blade coupled to the second arm. The retraction system also includes a second retraction assembly, the second retraction assembly including a carriage configured to engage a blade post having a blade coupled to a distal end and a handle coupled to a proximal end, the blade post adjustable relative to the carriage. The retraction system also includes a third retractor blade coupled to the blade post.

Alternatively or additionally to any of the embodiments in this section, an adaptor having a first region configured to engage the rack and a second region configured to engage the carriage.

Alternatively or additionally to any of the embodiments in this section, wherein the adaptor is configured to rotate relative to the rack; and wherein the adaptor is configured to translate relative to the rack.

Alternatively or additionally to any of the embodiments in this section, wherein the adaptor is fixed to the rack.

Alternatively or additionally to any of the embodiments in this section, wherein the adaptor includes a clamping mechanism configured to releasably secure the adaptor to the rack.

Alternatively or additionally to any of the embodiments in this section, wherein the adaptor includes an aperture; and wherein the rack extends through the aperture.

Alternatively or additionally to any of the embodiments in this section, wherein the carriage includes a projection, and wherein the adaptor includes a groove configured to engage the projection.

Alternatively or additionally to any of the embodiments in this section, wherein the projection is configured to translate within the groove of the adaptor.

Alternatively or additionally to any of the embodiments in this section, wherein translation of the projection within the groove of the adaptor moves the third retractor blade in a cranial-caudal direction relative to a patient.

Alternatively or additionally to any of the embodiments in this section, wherein the third retractor blade is configured to retract away from the first retractor blade and the second retractor blade to establish an operative corridor anterior to the psoas.

Alternatively or additionally to any of the embodiments in this section, wherein the first retractor blade and the second retractor blade are configured to translate along a first plane; wherein the third retractor blade is configured to retract along a second plane relative to the first plane; and wherein retraction of the third retractor blade is configured to establish an operative corridor anterior to the psoas.

Another example retraction system for accessing the spine of a patient from an anterior-to-psoas approach includes a first retraction assembly having a first retractor blade assembly and a second retractor blade assembly, a second retraction assembly having a third retractor blade assembly, wherein the first retraction assembly is coupled to the second retraction assembly such that adjustment of the first retractor blade assembly, the second retractor blade assembly or the third retractor blade assembly establishes an anterior-to-psoas operative corridor.

Alternatively or additionally to any of the embodiments in this section, further comprising an adaptor configured to couple the first retraction assembly to the second retraction assembly.

Alternatively or additionally to any of the embodiments in this section, wherein retraction of the second retraction assembly in an anterior direction relative to the first retraction assembly expands the operative corridor.

Alternatively or additionally to any of the embodiments in this section, wherein retraction of the third blade assembly in an anterior direction relative to the first retraction assembly expands the operative corridor.

Alternatively or additionally to any of the embodiments in this section, wherein retraction of the third retractor blade assembly in an anterior direction relative to the first retractor blade assembly, the second retractor blade assembly or both the first and second retractor blade assemblies expands the operative corridor.

Alternatively or additionally to any of the embodiments in this section, wherein the adaptor is configured to translate relative to the first retraction assembly.

Alternatively or additionally to any of the embodiments in this section, wherein the adaptor is configured to rotate relative to the first retraction assembly.

Alternatively or additionally to any of the embodiments in this section, wherein the adaptor is releasably adjustable relative to the first retraction assembly.

An example method for accessing the spine of a patient from a position anterior to the psoas includes dissecting to the spine of a patient along an anterior to psoas approach to form an operative corridor, inserting a first retractor blade coupled to a first arm into the operative corridor, inserting a second retractor blade coupled to a second arm into the operative corridor, expanding the operative corridor by moving one or both of the first arm and the second arm along a rack of a surgical retraction assembly, inserting a third retractor blade coupled to a blade post and a handle into the operative corridor, expanding the operative corridor with the third retractor blade, and after expanding the operative corridor with the third retractor blade, coupling the blade post to a carriage of the surgical retraction assembly.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
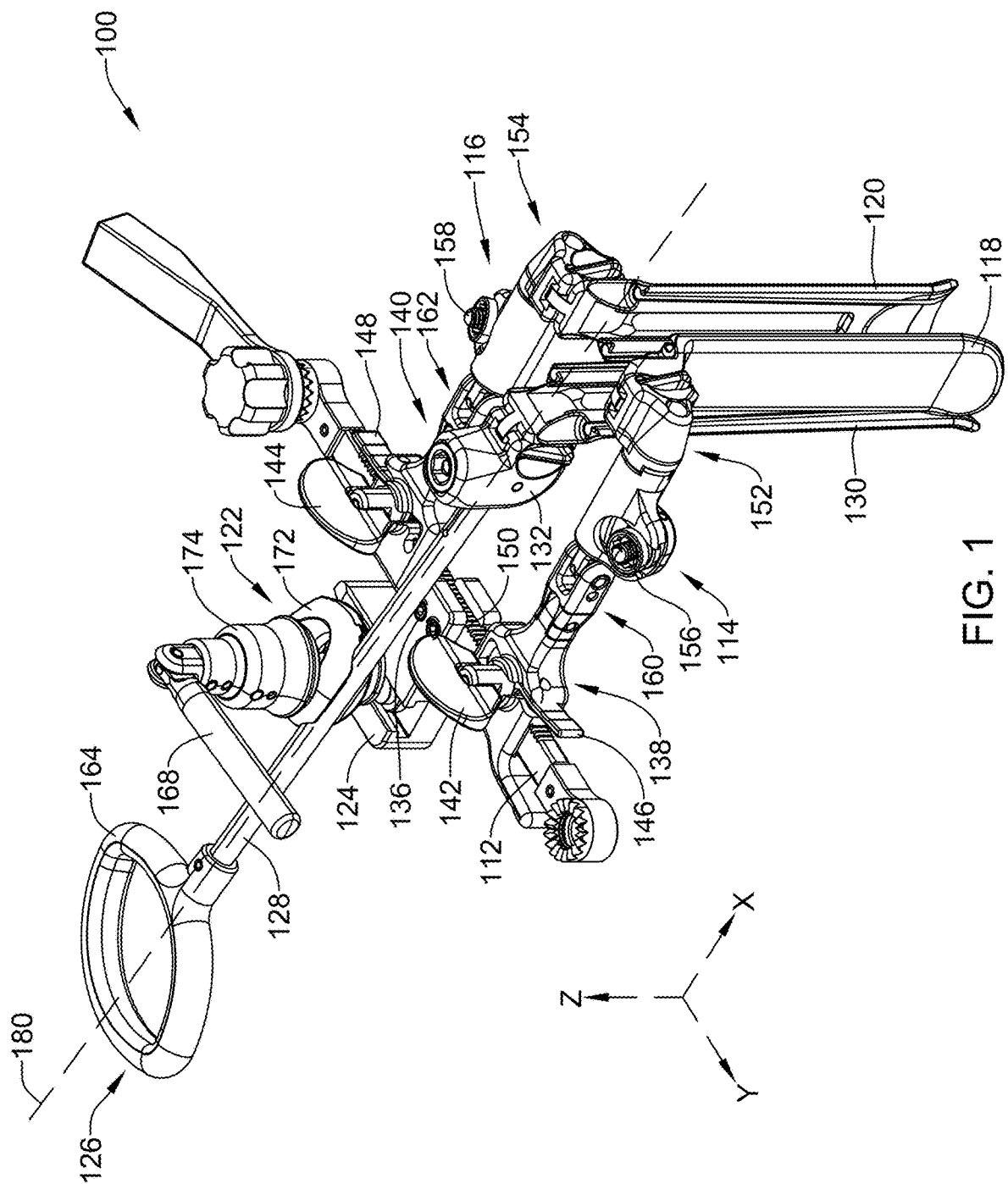
FIG. 1 illustrates a perspective view of an example surgical retractor system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The spine provides mobility, support, and balance. For example, the spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

A number of medical procedures, such as spinal surgeries, may be performed to address a variety of spinal conditions. For example, spinal fusion is a medical procedure performed to reduce the symptoms of damaged spinal discs, or for any pathology that would suggest direct spinal decompression as a treatment. The primary goals of spinal fusion procedures are to provide stability between the vertebrae on either side of the damaged disc and to promote natural fusion of those adjacent vertebrae. In some instances, a spinal fusion procedure is performed via an "open" approach, requiring an incision and retraction of tissue to access a targeted portion of the spine. One open approach may include accessing the spine from a position anterior to the psoas muscle. This surgical procedure may utilize a surgical retraction system positioned anterior to a patient's spine. The surgical retraction system may manipulate one or more surgical retraction blades to create a surgical operative corridor through which a clinician may introduce additional medical devices to treat the spinal condition. A need therefore exists for improvements relating to the performance of surgical retraction systems. The systems and methods described herein are directed to addressing these needs.

The present application describes a tissue retraction system and related instruments and methods for performing minimally invasive spinal surgery. The tissue retraction system (e.g., a retractor) may use one or more retractor blades to establish and maintain an operative corridor to the surgical target site. FIG. 1 is a perspective view of a portion of an example surgical retraction system 100. The system 100 may include a rack 112, a first arm 114, a second arm 116, a first retractor blade 118 removably attached to a first end of the first arm 114 and a second retractor blade 120 removably attached to a first end of the second arm 116. Additionally, the illustrated surgical system 100 may also include a carriage 122 coupled to the rack 112, such as via an adaptor 124. The carriage 122 may be designed to engage a retraction assembly 126. The retraction assembly 126 may include a third retractor blade 130 coupled to a first end of a blade post 128. A handle 164 may be attached to a second end (opposite the first end) of the blade post 128. As will be described in greater detail herein, in operation, the first retractor blade 118, the second retractor blade 120 and the third retractor blade 130 may establish and define an operative corridor through which access to a surgical target site is achieved. This operative corridor may expandable in a caudal-cranial direction as well as anteriorly.

The following describes the first arm 114 and the second arm 116, which can be virtually identical in form and function. For example, FIG. 1 illustrates that each of the arms 114, 116 may include a proximal portion 138, 140 (also shown in FIG. 3). Each of the proximal portions 138, 140 may include an aperture configured to receive the rack 112 such that the rack 112 and each proximal segment 138, 140 are generally perpendicular to one another. Accordingly, in operation, each the of the arms 114, 116 may translate in either direction along the longitudinal axis of the rack 112.

FIG. 1 further illustrates that the rack 112 is generally an elongated member having a plurality of teeth 150 distributed on one of its sides. The teeth 150 are configured to interact with the proximal portions 138, 140 described above to allow controlled translation of the arms 114, 116. FIG. 1 illustrates that the rack 112 may include a rectangular cross-sectional shape. However, the rack 112 may include other cross-sectional shapes. For example, the cross-sectional shape of the rack 112 may be circular, ovular, square, triangular, polygonal, or the like.

FIG. 1 further illustrates that the proximal portions 138, 140 of each of the arms 114, 116 may each include a translator to affect the translation of the arms 114, 116 along the rack 112. In the illustrated example, the translator is in the form of a thumb tab 142, 144. Each thumb tab 142, 144 may be rotatable to control the directional translation (e.g., in a caudal or cranial direction) of each arm 114, 116 along the rack 112. The translator can take other forms in other implementations.

Additionally, each of the arms 114, 116 may include a pawl 146, 148 which is actuatable from a first (e.g. "unlocked") position to a second (e.g. "locked") position. Each pawl 146, 148 may be configured to engage teeth 150 of the rack 112. Engagement of either the first pawl 146 or second pawl 148 with the teeth 150 may directly prevent translation of either the first arm 114 or the second arm 116 when the respective pawl 146, 148 is in the locked position. However, when a pawl 146, 148 is in the first unlocked position, the pawl 146, 148 disengages from the teeth 150, thereby allowing free translation of its respective arm 114, 116 along the rack 112. For example, the pawls 146, 148 may be ratcheting, such that the thumb tab 142 may be rotated clockwise to translate the first arm 114 relative to the second arm 116 without depressing the pawl 146. The pawl 146 prevents the thumb tab 142 from rotating counterclockwise unless the pawl 146 is depressed. Likewise, the thumb tab 144 may be rotated counterclockwise to translate the second arm 116 relative to the first arm 114 without depressing the pawl 148. The pawl 148 prevents the thumb tab 144 from rotating clockwise unless the pawl 148 is depressed.

FIG. 1 further illustrates that each arm 114, 116 may include a distal portion 152, 154. The distal portion 152, 154 of each arm 114, 116 may be connected to each of the retractor blades 118 and 120. For example, FIG. 1 illustrates that the distal portion 152 may be releasably attached to the first retractor blade 118. Similarly, the distal portion 154 may be releasably attached to the second retractor blade 120.

Rotation of the distal portions 152, 154 of each arm 114, 116, respectively, may rotate the retractor blade to which the respective arm 114, 116 is releasably attached. For example, rotation (e.g., clockwise or counterclockwise) of the distal portion 152 may rotate the first retractor blade 118 clockwise or counterclockwise, respectively, while rotation of the of the distal portion 154 may rotate the second retractor blade 120 clockwise or counterclockwise.

In some implementations, the distal portions 152, 154 of each arm may include features to adjust the depth of the entire blades 118, 120 coupled thereto. An example implementation of such a feature is shown in more detail in FIG. 9, infra.

FIG. 1 further illustrates that the distal portion 152, 154 of each arm 114, 116 may further include a splay unit 156, 158. Each splay unit 156, 158 may be designed to permit continuous variable blade splay and will actuate, for example, to allow for up to 45° (or any other suitable degree) of angular blade splay. Blade splay may expand the distal operative corridor without expanding the proximal operative corridor (and thereby necessitating a larger skin incision).

FIG. 1 further illustrates that each arm 114, 116 may include a pivotable linkage 160, 162 (e.g., a double hinge) coupled to and spanning between the proximal portion 138, 140 and the distal portion 152, 154 of each arm 114, 116, respectively. This pivotable linkage 160, 162 may create a flexible arm construct such that the arms 114, 116 can pivot about and adjust to reduce blade skew and blade height issues (encountered when facing difficult patient anatomy).

As described herein, FIG. 1 illustrates that the system 100 may further include a retraction assembly 126. The retraction assembly 126 may include an elongated blade post 128 releasably engaged to a carriage 122. The retraction assembly 126 may further include a third retractor blade 130 attached to the blade post 128 via a blade holder 132. Further, the blade post 128 is also connected to a blade post handle 164 that allows the blade post 128 to be manually translated along its own longitudinal axis 180 and to be manually rotated around its own longitudinal axis 180 ("roll").

FIG. 1 includes a three-dimensional coordinate system which shows axis lines X, Y and Z, oriented as shown by the arrows. This coordinate system depicts general relative directions of coordinate system axes of particular components referred to herein.

In the context of this discussion of the blade post 128, the longitudinal axis 180 of the blade post 128 may be considered the "x-axis". Accordingly, if the longitudinal axis 180 represents the x-axis of the blade post 128, rotation around the x-axis of the blade post 128 is "roll," rotation around the corresponding z-axis (relative to the x-axis of the blade post 128) is "yaw," and rotation around the corresponding y-axis (relative to the x-axis and z-axis of the blade post 128) is "pitch."

As discussed herein, the retraction assembly 126 may be coupled to a carriage 122 which is further coupled to the rack 112 via the adaptor 124. The carriage 122 functions to connect the third retractor blade 130 to the rack 112 via the blade post 128 on which the third retractor blade 130 may be releasably attached. The carriage 122 may include a manual lever arm 168 which is actuatable by rotating either clockwise or counterclockwise to tighten and loosen the carriage between a "locked" and an "unlocked" position.

Figure 2:
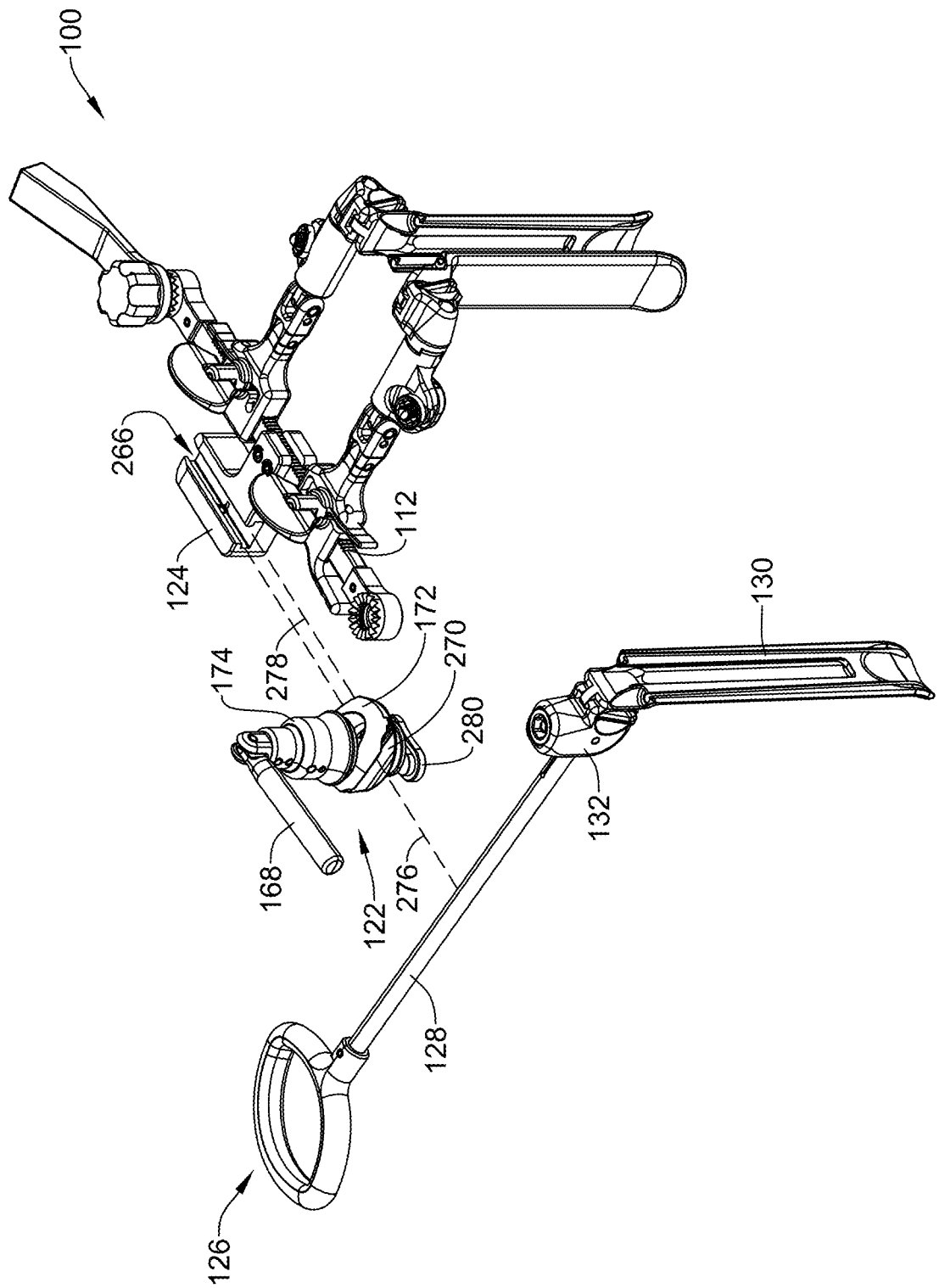
FIG. 2 illustrates a partial exploded view of the example surgical retractor system depicted in FIG. 1.

Referring to FIG. 2, the carriage 122 may translate through a groove 266 in the adaptor 124 while also permitting the blade post's 128 orientation to be manipulated while the manual lever arm 168 is loosened in an unlocked configuration. Further, the carriage 122 illustrated in FIG. 1 may be designed to permit the blade post 128 to move with five degrees of freedom (translation in two dimensions as well as yaw, pitch, and roll rotational motion). For the purposes of this discussion, yaw refers to rotation about a vertical axis extending through the carriage 122 (e.g., a z-axis of the carriage 122), pitch refers to rotation about an axis parallel to the rack 112 (e.g., a y-axis of the carriage 122), and roll refers to rotation about an axis that intersects the rack 112 at the location of the carriage 122 (e.g., an x-axis of the carriage 122). In examples in which the carriage does not translate vertically along an axis extending through the carriage 122, up and down movement of the blade 130 may be accomplished via simultaneous pitch of the carriage 122 and "toeing" (e.g., pivoting) the blade holder 132. The illustrated embodiment shows the carriage 122 configured for translation along the groove 266 (shown in FIG. 4), as explained herein. Additionally, the blade post 128 may translate along its own longitudinal axis by moving back and forth (e.g., in an anterior-posterior direction) in a post channel 270 (shown in FIG. 2), which can also be locked via the manual lever arm 168.

Additionally, the carriage 122 may be designed to translate in a direction of the z-axis illustrated in FIG. 1. Accordingly, in examples in which the carriage 122 may translate vertically along the z-axis extending through the carriage 122, the up and down movement of the blade 130 may be accomplished via translation of the carriage along its vertical axis.

FIG. 1 further illustrates that the carriage 122 may include a blade post holder 172 that can yaw, pitch, and roll when the manual lever arm is in an unlocked position. In the example shown, the proximal surface of the blade post holder 172 is partially spherical, and forms a ball joint connected with a post holder compressing body 174. The post holder compressing body 174 has a complementary distal surface that mates with the proximal surface of the post holder 172. These surfaces may be roughened to allow them to articulate relative to one another when not under any compression, but to be firmly locked into position when under compression.

Actuation of the manual lever arm 168 between an unlocked and a locked position may impart a compressive force exerted by the post holder compressing body 174 onto the blade post holder 172. The blade post 128 may be locked in position relative to the carriage 122 when a compressive force is exerted by the blade post holder compressing body 174 on the proximal surface of the blade post holder 172. Additionally, this compressive force also causes the post holder 172 to pinch the post channel 270 (shown in FIG. 2), thereby holding the blade post 128 in place and preventing the blade post 128 from translating along its longitudinal axis.

Additionally, the compressive force exerted by the blade post holder 172 may also exert a distally directed compressive force on a distal portion of the carriage member 122 which prevents the translation of the carriage 122 along the groove 266 of the adaptor 124. In short, the mechanism shown in the figures utilizes a distally directed compressive force on the proximal surface of the post holder 172 to arrest movement of the blade post 128 relative to the carriage 122 and movement of the carriage 122 relative to the rack 112.

The first retractor blade 118, the second retractor blade 120 and the third retractor blade 130 may be of any configuration that is known to be suitable in the art. In the illustrated embodiments, the retractor blades 118, 120, 130 may be substantially vertical (i.e., extend in the proximal/distal axis) with a distal curved portion. For example, the first retractor blade 118 may include a distal curved portion that curves back toward the caudal direction, the second retractor blade 120 may include a distal curved portion that curves back toward the cranial direction, and the third retractor blade 130 may include a distal curved portion that curves back toward the anterior direction (e.g., toward the rack 112).

Each of the first retractor blade 118, the second retractor blade 120 and the third retractor blade 130 may be releasably attached to the arm 114, arm 116 and blade post 128, respectively. Accordingly, a user may customize the size of the first retractor blade 118, the second retractor blade 120 and the third retractor blade 130. For example, FIG. 1 illustrates that the first retractor blade 118, the second retractor blade 120 and the third retractor blade 130 of the surgical system 100 are substantially equal in length. However, a user may swap out the first retractor blade 118, the second retractor blade 120 and the third retractor blade 130 to include blades having varying lengths, depending on the nuances of a given approach to a medical procedure. A user may include a clinician, physician, surgeon, nurse, or other professional practitioner. For example, during an anterior-to-psoas approach, a user may elect to customize the length, width, shape, curvature, etc. of the first retractor blade 118, the second retractor blade 120 and the third retractor blade 130 to best match a patient's particular anatomical characteristics.

Additionally, when positioned adjacent the spine of a patient, the first retractor blade 118 may face the second retractor blade 120, whereby the distal end of the first retractor blade 118 may curve in a caudal direction and the distal end of the second retractor blade 120 may curve in a cranial direction. Additionally, the face of the third retractor blade 130 may be positioned substantially perpendicular to the first blade 118 and second blade 120, whereby the distal end of the third retractor blade 130 may curve in an anterior direction (e.g., away from the patient's spine). As discussed in greater detail below, the orientation of the first retractor blade 118, the second retractor blade 120 and the third retractor blade 130 may permit the expansion of an operative corridor in a caudal direction, cranial direction and anterior direction.

FIG. 2 illustrates a partially exploded view of the example surgical system 100 including the carriage 122 spaced away from the adaptor 124 (FIG. 2 illustrates the adaptor 124 remaining attached to the rack 112). FIG. 2 further illustrates the retraction assembly 126 spaced away from the carriage 122. As described herein, the retraction assembly 126 includes the blade post 128 attached to the third retractor blade 130 via the blade holder 132. Blade holder 132 may be designed to permit the third retractor blade 130 to pitch relative to the blade post 128.

FIG. 2 further illustrates that the blade post 128 may be releasably secured within a post channel 270 located on the blade post holder 172 (the dashed line 276 depicts the alignment of the blade post 128 with the post channel 270), whereby actuation of the manual lever arm 168 may cause the post holder compressing body 174 to exert a compressive force onto the blade post holder 172. This compressive force may, in turn, cause the post holder 172 to clamp down on the blade post 128 (e.g., the diameter of the channel 270 is reduced), thereby arresting the blade post 128 from translating along or rotating around its longitudinal axis.

FIG. 2 further illustrates the carriage 122 spaced away from the adaptor 124. The carriage 122 may include a distally extending projection 280 which may be designed to translate within the groove 266 of the adaptor 124. The dashed line 278 depicts the alignment of the projection 280 with the groove 266 of the adaptor 124. In operation, the translation of the carriage 122 along the groove 266 may translate the third retractor blade 130 along an axis parallel to the rack 112. For example, the third retractor blade 130 may translate in a caudal-cranial direction as the projection 280 translates within the groove 266. Actuation of the manual lever arm 168 between a locked and unlocked configuration may permit the projection 280 to translate within the groove 266 (when in an unlocked configuration) or prevent the carriage 122 from sliding within the groove 266 (when in a locked configuration).

Additionally, while the illustrated surgical system 100 includes the adaptor 124 releasably attached to the rack 112, the surgical system 100 may include an embodiment which does not include the adaptor 124. For example in some instances, the carriage 122 may be directly attached to the rack 112. The rack 112 may include a groove similar in form and function to the groove 266 of the adaptor 124. Accordingly, in this example, the projection 280 of the carriage 122 may extend directly into a groove located on the rack 112. Further, the carriage 122 may translate within a groove located on the rack 112 in a manner like that described herein with respect to the projection 280 translating within the groove 266 of the adaptor 124.

Figure 3:
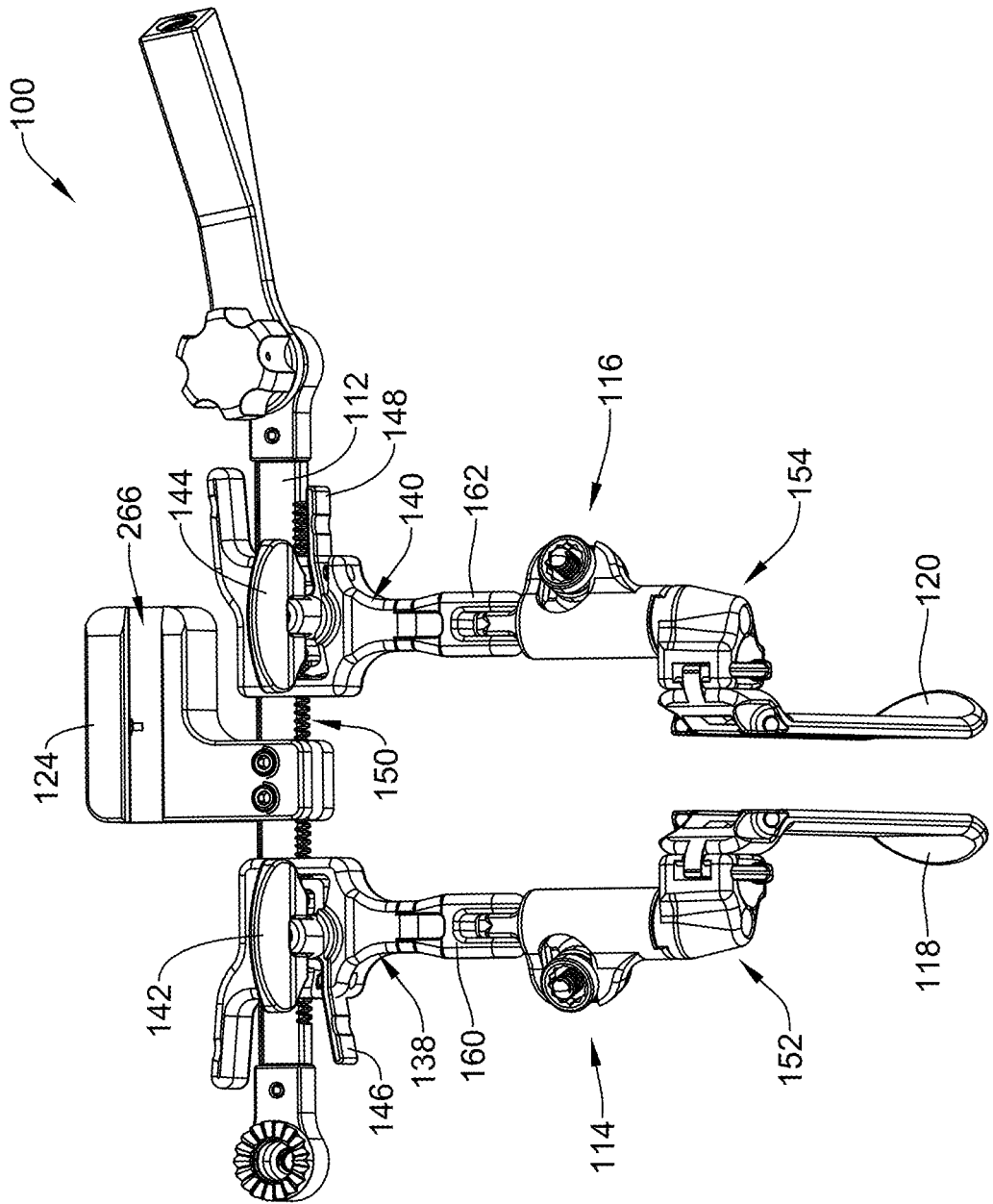
FIG. 3 illustrates a top view of a portion of the example surgical retractor system depicted in FIG. 1.

FIG. 3 is a top view of a portion of the example surgical system 100. For clarity, the carriage 122 and retraction assembly have been omitted from FIG. 3. As described herein, FIG. 3 illustrates the first arm 114 and the second arm 116 attached to the rack 112. The first arm 114 includes the proximal portion 138, the pivotable linkage 160 and the distal portion 152. Similarly, the second arm 116 includes the proximal portion 140, the pivotable linkage 162 and the distal portion 154. Each of the proximal portions 138, 140 include and aperture through which the rack 112 extends. As discussed herein, each arm 114, 116 also include a thumb tab 142, 144, the rotation of which permits the translation of the arms 114, 116 along the rack 112. Additionally, FIG. 3 illustrates that each arm 114, 116 also includes a pawl 146, 148 actuatable from a first (e.g. "unlocked") position to a second (e.g. "locked") position. Each pawl 146, 148 may be configured to engage the teeth 150 of the rack 112 to prevent translation of the either the first arm 114 or the second arm 116 when the respective pawl 146, 148 is in a "locked" position. However, when a pawl 146, 148 is in an "unlocked" position, the pawl 146, 148 disengages from the teeth 150, thereby allowing free translation of its respective arm 114, 116 along the rack 112.

FIG. 3 also illustrates the first retractor blade 118 releasably attached to the distal portion 152 and the second retractor blade 120 releasably attached to the distal portion 154. The first retractor blade 118 may face the second retractor blade 120, whereby the distal end of the first retractor blade 118 may curve in a caudal direction and the distal end of the second retractor blade 120 may curve in a cranial direction. Additionally, the distal ends of the first retractor blade and second retractor blade 118, 120 may be flat. As will be discussed in greater detail below, the orientation of the first retractor blade 118 with respect to the second retractor blade 120 may permit the expansion of an operative corridor in a caudal-cranial direction.

Figure 4:
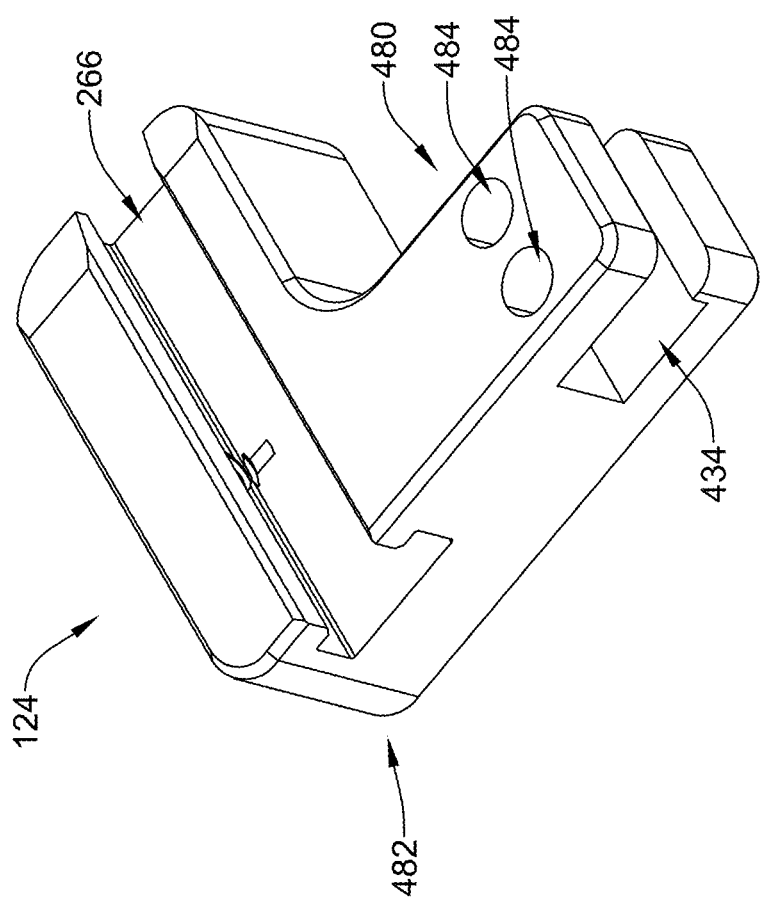
FIG. 4 illustrates a perspective view of an adaptor of the example surgical retractor system depicted in FIG. 1.

FIG. 4 is a perspective view of the adaptor 124. The adaptor 124 may include a first end region 480 and a second end region 482. The first region 480 may include an aperture 434 (e.g., channel, opening, etc.) sized to permit the rack 112 to extend therethrough. In some instances, the shape of the aperture 434 may be designed to match the cross-sectional shape of the rack 112. For example, the shape of the aperture 434 shown in FIG. 4 may be designed to match the rectangular cross-sectional shape of the rack 112. As discussed herein, the aperture 434 may include a variety of different shapes. For example, the aperture 434 may be substantially circular, ovular, square, triangular, polygonal, or the like. An example rack 112 designed with a circular cross-sectional shape may permit the adaptor 124 to rotation around the longitudinal axis of the rack 112.

The adaptor 124 may include the aperture 434 (e.g., a first channel) extending laterally therethrough. The aperture 434 may be sized and dimensioned to receive the rack 112. Additionally, FIG. 4 illustrates that the adaptor 124 may releasably secured to the rack via one or more attachment members 136 (e.g., bolt, screw, pin, clamp, etc.). In some examples, the adaptor 124 may be fixedly attached to the rack 112 such that an additional instrument (e.g., screwdriver, etc.) is required to loosen and reposition it along the longitudinal axis of the rack 112. However, in other examples, the adaptor 124 may be designed to include a "quick release" feature, whereby a user may easily release and reposition the adaptor 124 along the longitudinal axis of the rack 112. For example, the adaptor 124 may include a lever, switch, button, tab, knob, clamp, etc. that may be actuated by a user to release and reposition the adaptor 124 along the longitudinal axis of the rack 112.

FIG. 4 further illustrates that the first end region 480 may include one or more apertures 484 which permit a fastener (e.g., bolt, pin, etc.) to extend therethrough. The fastener may be designed to fixedly attach the adaptor 124 to the rack 112. In some examples, the adaptor 124 can further include one or more features for adjustability of the adaptor 124 along the rack 112. For instance, the adaptor 124 can include a pinion actuatable by the user to crawl the adaptor 124 along the rack 112.

FIG. 4 further illustrates that the second end region 482 may include a groove 266 extending laterally across a proximal surface of the adaptor 124. In some examples, the groove 266 may be designed to allow the projection 280 of the carriage 122 to translate within the groove 266, while constraining the projection 280 from departing from the groove 266. In one example, the cross-sectional profile of the groove 266 may include a cross-sectional profile of an inverted letter T, in which the stem of the T intersects the proximal surface of the adaptor 124. Further, the projection 280 of the carriage 122 could engage the groove 266 by having a complementary shape (e.g., a narrow stem and a broad base resembling an inverted T). Such a configuration would allow the carriage 122 to translate along the groove 266, but would constrain the carriage 122 from leaving the groove 266. The groove 266 may include a variety of shapes, including, but not limited to a keyhole shape and a triangular shape.

As discussed herein, spinal fusion procedures are routinely performed using an open approach, requiring an incision and retraction of tissue to access a targeted portion of the spine. A variety of open approaches have been developed. For example, open approaches such as anterior lumbar interbody fusion (ALIF), posterior lumbar interbody fusion (PLIF), and transforaminal lumbar interbody fusion (TLIF) have been developed to treat complications such as low back and leg pain. While these approaches may be appropriate in certain circumstances, they may also pose significant constraints. Gaining clear access to the spine, for both visualization and treatment of the affected vertebrae, is one aspect of spinal fusion surgery, and there are several different approaches a surgeon typically takes for an interbody-type procedure. Factors that influence a surgeon's decision on which approach to take may include the spinal condition to be treated, the location of the surgical target site in the spinal column, and the patient's overall health. In some instances, certain approaches may cause the disruption of the surrounding soft tissues, nerves and blood vessels of the targeted portion of the spine.

However, one approach, called the anterior-to-psoas approach, may permit access to the targeted area of the spine while potentially minimizing disruption of the surrounding soft tissues, nerves and blood vessels. The anterior-to-psoas approach is different from other interbody fusion techniques in that to approach the spine, the surgeon makes a small incision in the skin of the patient's anterolateral space, partially between the patient's side and the patient's abdomen. Then, using minimally invasive surgical techniques, the surgeon creates an operative corridor through the underlying soft tissues, between the peritoneum and the psoas muscle, until reaching the spine. Advantages to this approach include that neuromonitoring is not explicitly required, the operative corridor does not traverse the psoas muscle and lumbar plexus (as is performed in a traditional lateral transpsoas approach procedure, for example), the approach obviates the problem of bony anatomy (e.g., the iliac crest) obstructing the approach (as is the case with lateral transpsoas approaches at L4/L5), and the approach reduces the retraction of major blood vessels (as is done with an ALIF approach).

Different approaches may utilize different retraction systems specifically tailored for a particular approach. However, retraction systems utilized for approaches other than the anterior-to-psoas approach may not work to perform an anterior-to-psoas spinal surgery. The retraction systems disclosed herein are designed to create an operative corridor when utilizing an anterior-to-psoas approach during a spinal surgery. For example, when creating the operative corridor through the underlying soft tissues during an anterior-to-psoas approach for a spinal surgery, the surgical system 100 may provide a single system (versus utilizing several retractor components that are anchored or individually held-in-place during the interbody procedure) to maintain the operative corridor that has sufficient degrees of freedom and fixation to create and maintain a desired operative corridor to a surgical target site during the spinal surgery.

FIGS. 5-8 illustrate a method for performing minimally invasive spinal surgery using the surgical system 100 and related examples described herein. In particular, FIGS. 5-8 describe the surgical system 100 utilized to perform an anterior-to-psoas spinal surgery. The surgical system 100, in particular, may be utilized to establish and maintain an operative corridor to the surgical target site.

Figure 5:
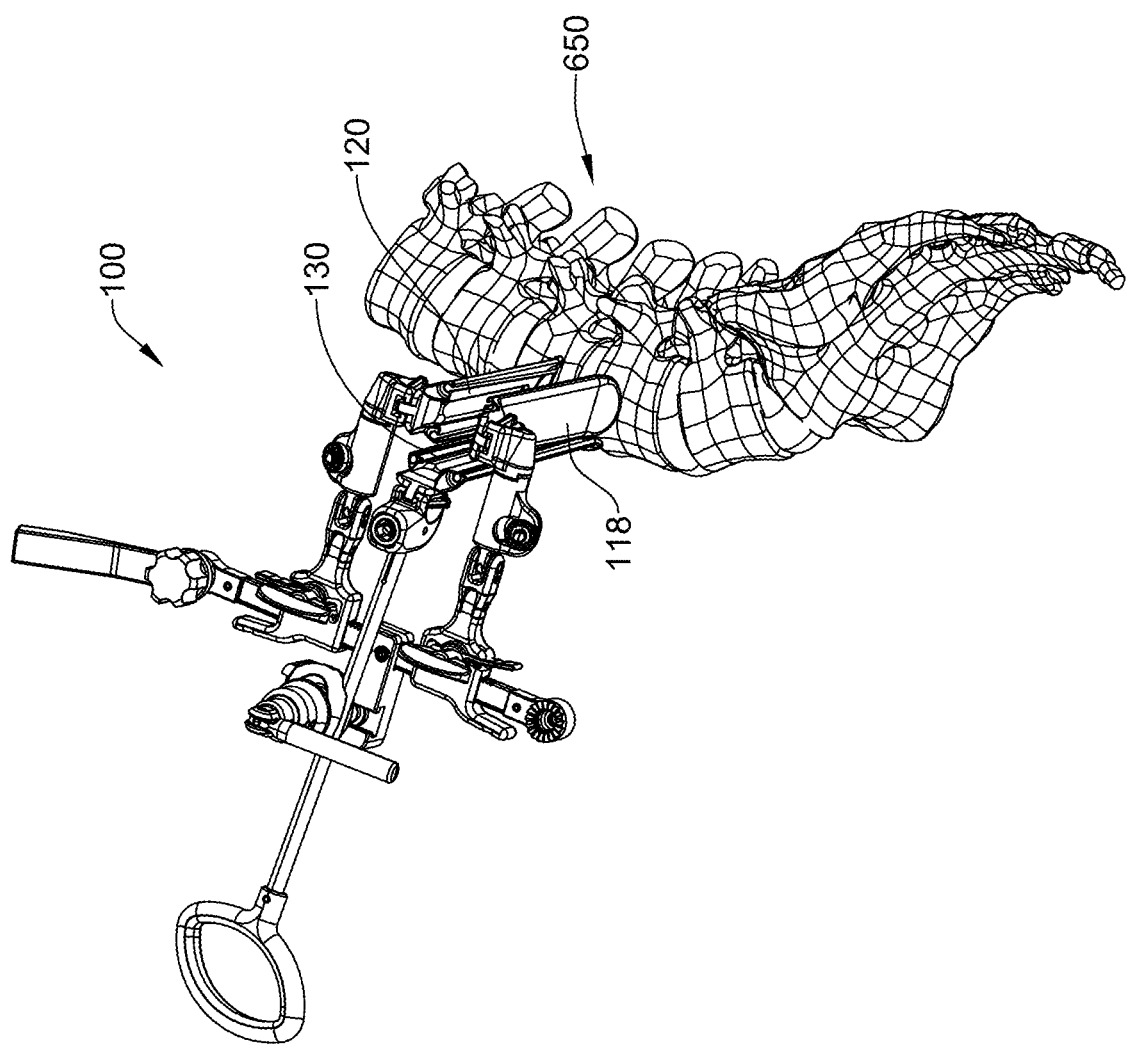
FIG. 5 depicts a perspective view of an example surgical retractor system positioned adjacent a spine.

FIG. 5 illustrates the surgical system 100 positioned anterior to the direct lateral aspect of the lumbar spine 650 of a patient (for clarity, FIGS. 5-8 omit all but the lumbar spine 650 of the patient). Once positioned adjacent the surgical target site (e.g. an intervertebral disc of the lumbar spine 650), the first retractor blade 118, the second retractor blade 120 and the third retractor blade 130 may be inserted into a small incision made on a lateral aspect of the patient's abdomen). In some methods, the first retractor blade 118, the second retractor blade 120 and the third retractor blade 130 may be inserted into the incision simultaneously. In other methods, the first retractor blade 118 and the second retractor blade 120 may be inserted simultaneously into the incision prior to the insertion of the third retractor blade 130. In yet other methods, the first retractor blade 118, the second retractor blade 120 and the third retractor blade 130 may be individually inserted into the incision in any order. In FIG. 5, neither the first retractor blade 118, the second retractor blade 120 nor the third retractor blade 130 have been retracted. A beneficial feature of the initial positioning of the retractor blades 118, 120, 130 as shown in FIG. 5 includes increased safety, tactile feedback, adjustability compared to other surgical retraction systems and improved visibility with the operative corridor (e.g., improved visibility when placing the blade 130). In particular, the numerous degrees of freedom on the blade 130 allow the blade 130 to be finely manipulated, which facilitates delicate tissue retraction. This is important because the blade 130 may retract the peritoneum, aorta, and the sympathetic chain, which are all delicate structures that, if damaged, could have catastrophic consequences.

Figure 6:
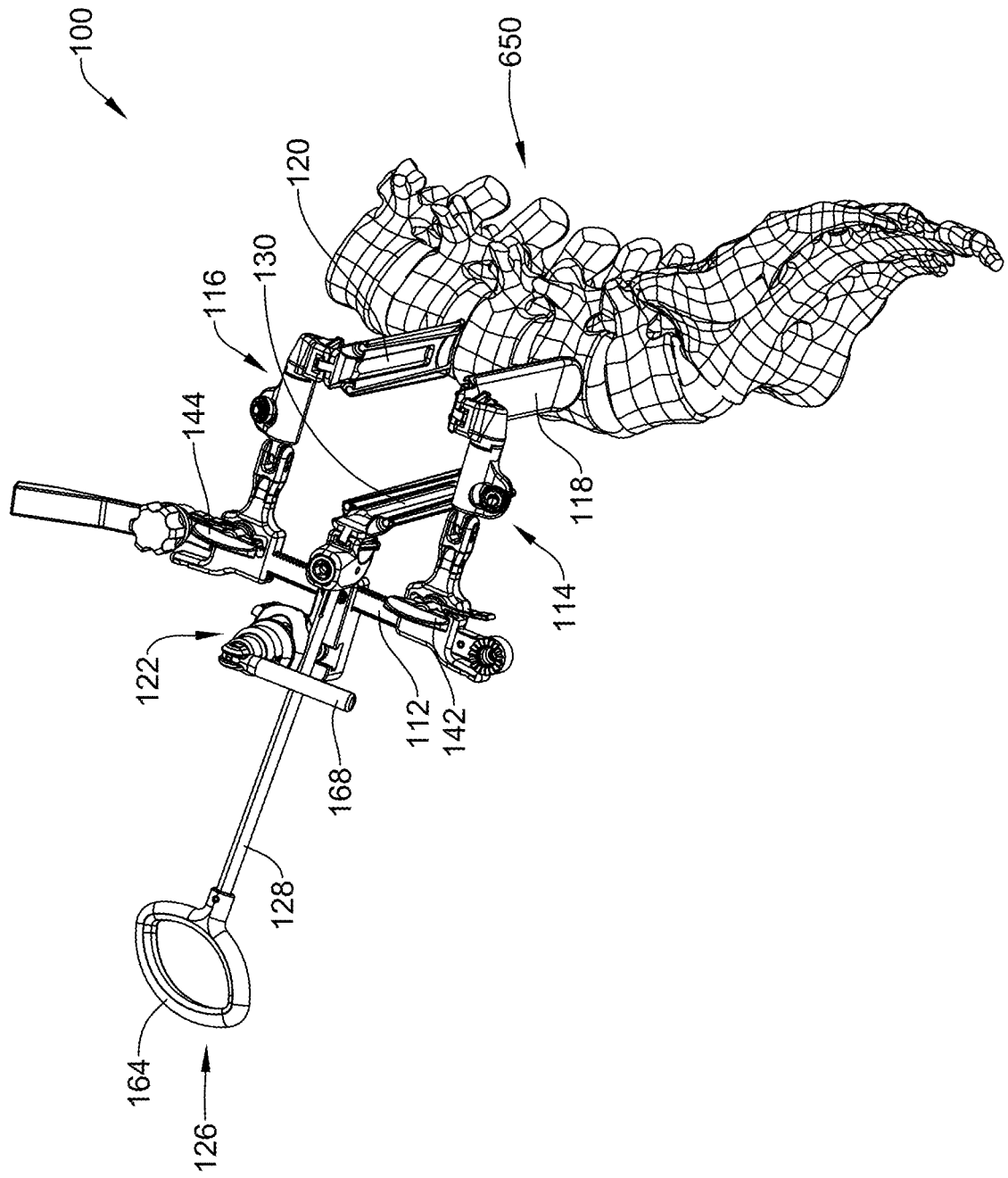
FIG. 6 depicts another perspective view of an example surgical retractor system positioned adjacent a spine.

FIG. 6 illustrates that after the distal end regions of the first retractor blade 118, the second retractor blade 120 have been inserted through the skin, one or more of the first retractor blade 118 and the second retractor blade 120 may be retracted along the rack 112 to expand the incision and establish an operative corridor to the targeted region of the spine 650. The operative corridor may be utilized to insert one or more medical instruments into the targeted region of the spine. For example, as discussed herein, a user may rotate the thumb tab 142 to translate the arm 114 and the first retractor blade 118 in a caudal direction. Similarly, the user may rotate the thumb tab 144 to translate the arm 116 and the second retractor blade 120 in a cranial direction.

After retraction of the first retractor blade 118 and the second retractor blade 120, a user may retract the third retractor blade 130 in an anterior direction (e.g., in a direction away from the patient's spine). In some examples, the user may manipulate the retraction assembly 126 independent of the carriage 122 (possibly grasping the handle 164) while retracting the third retractor blade 130 in the anterior direction. Once the desired amount of retraction has been performed and the operative corridor has been established, the user may insert the blade post 128 into the channel 270 (shown in FIG. 2) and actuate the manual lever arm 168 to a locked position to prevent the third retractor blade 130 from moving (e.g., longitudinally and rotationally) relative to the first retractor blade 118 and the second retractor blade 120. As the user utilizes the system 100 to expand the operative corridor (as shown in FIG. 6), any one of the first retractor blade 118, the second retractor blade 120 and the third retractor blade 130 may be manipulated along its five degrees of freedom (e.g., translation in two directions, in addition to its pitch, yaw and roll) to achieve the desired operative corridor.

Figure 7:
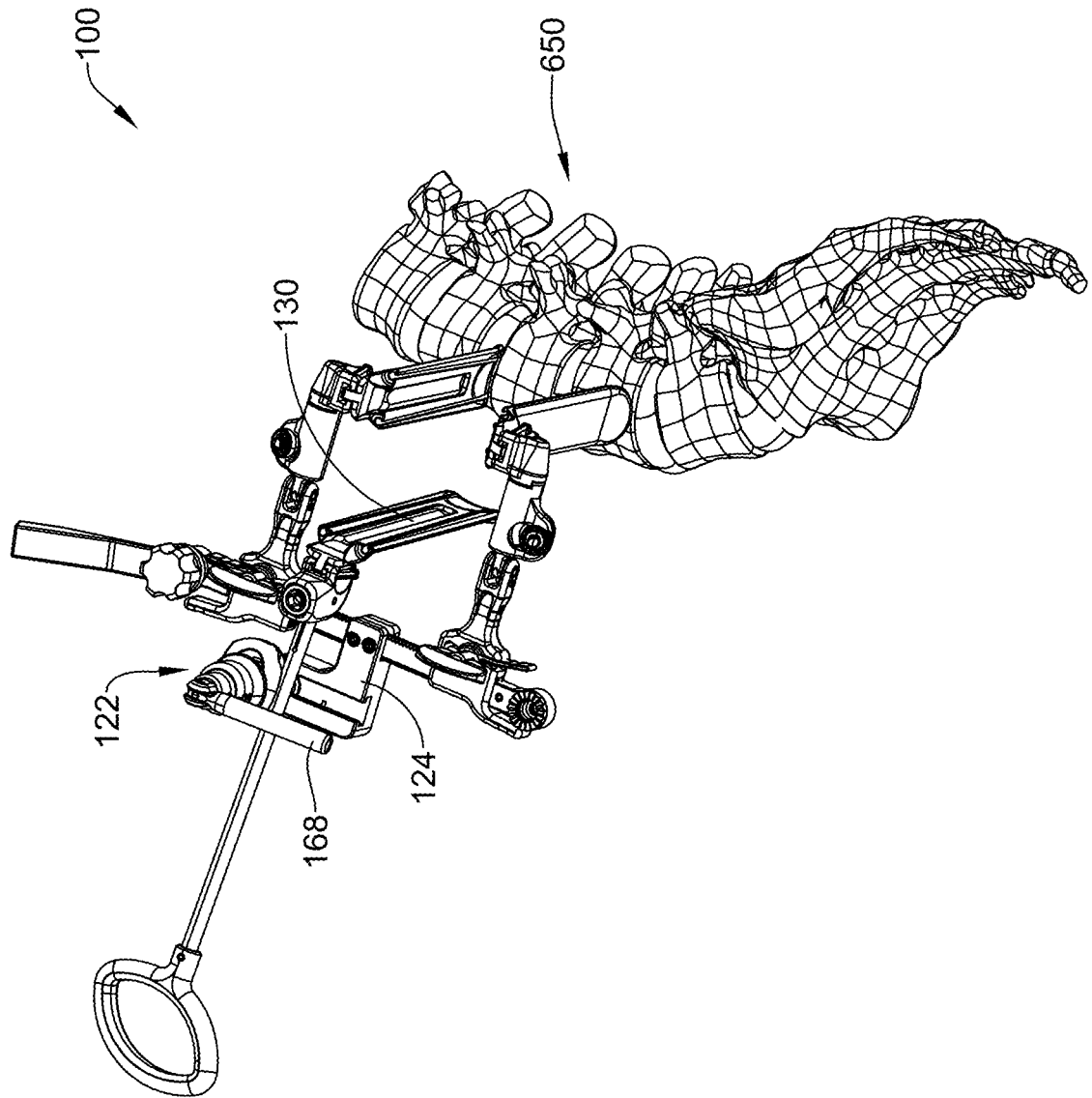
FIG. 7 depicts another perspective view of an example surgical retractor system positioned adjacent a spine.

FIG. 7 illustrates another beneficial aspect of the surgical system 100 whereby movement of the carriage 122 along the adaptor 124 allows a user greater flexibility to position the third retractor blade 130 within the operative corridor (or while expanding the operative corridor as described with respect to FIG. 6). Specifically, FIG. 7 illustrates that actuating the lever arm 168 from a locked to an unlocked position permits a user to move the carriage 122 along the adaptor 124 in a cranial direction, thereby permitting the third retractor blade 130 to move in a cranial direction within the operative corridor. As described herein, unlocking the lever arm 168 may also permit the third retractor blade 130 to be translated in an anterior-posterior direction in addition to being rotated around its longitudinal axis.

Figure 8:
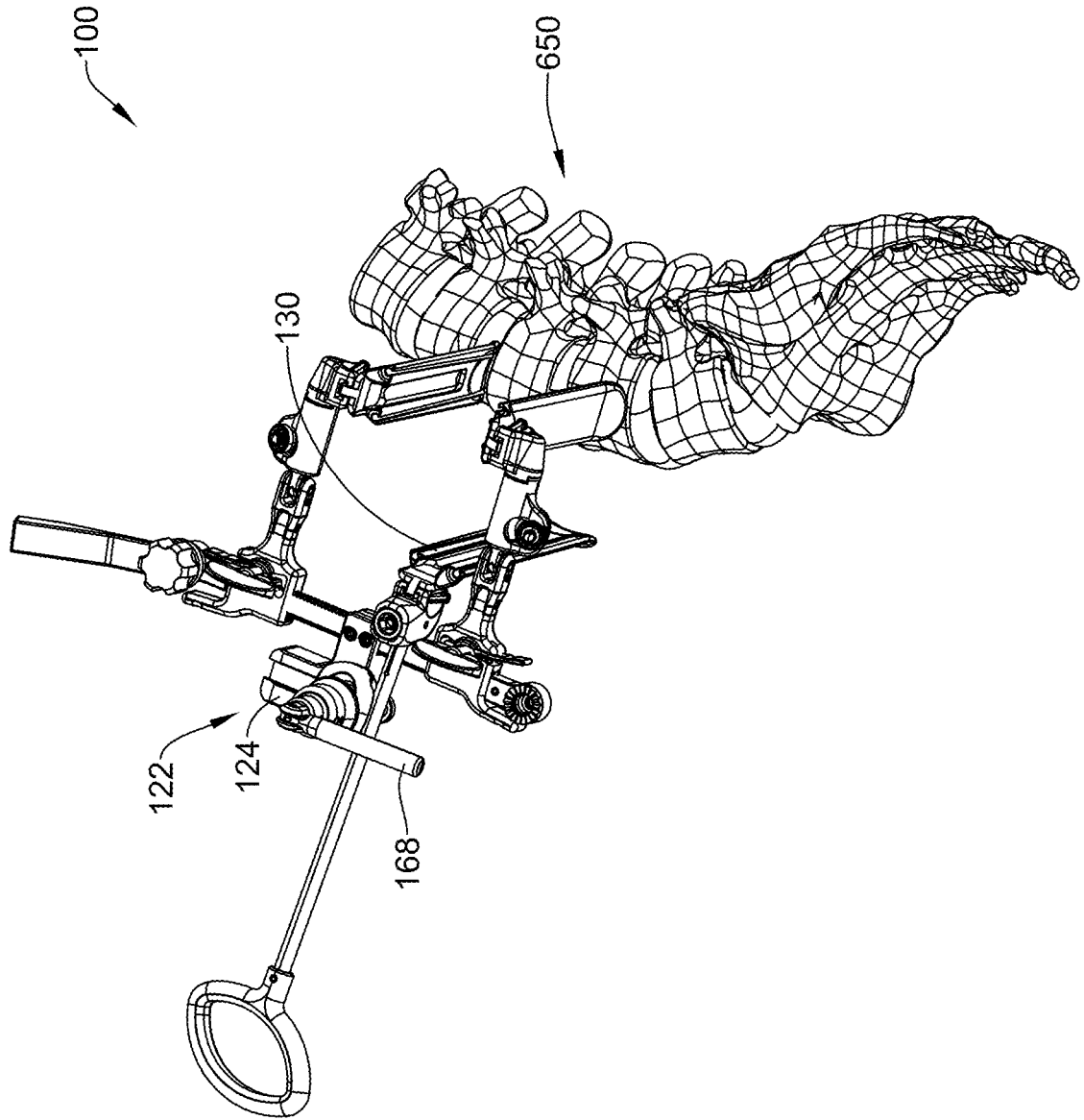
FIG. 8 depicts another perspective view of an example surgical retractor system positioned adjacent a spine.

Like FIG. 7, FIG. 8 illustrates that actuating the lever arm 168 from a locked to an unlocked position permits a user to move the carriage 122 along the adaptor 124 in a direction opposite to that shown in FIG. 7. In other words, actuating the lever arm 168 from a locked to an unlocked position permits a user to move the carriage 122 along the adaptor 124, thereby permitting the third retractor blade 130 to move in either a caudal or cranial direction within the operative corridor. As described herein, unlocking the lever arm 168 may also permit the third retractor blade 130 to be translated in an anterior-posterior direction in addition to being rotated around the longitudinal axis 180 of the blade post 128.

Figure 9:
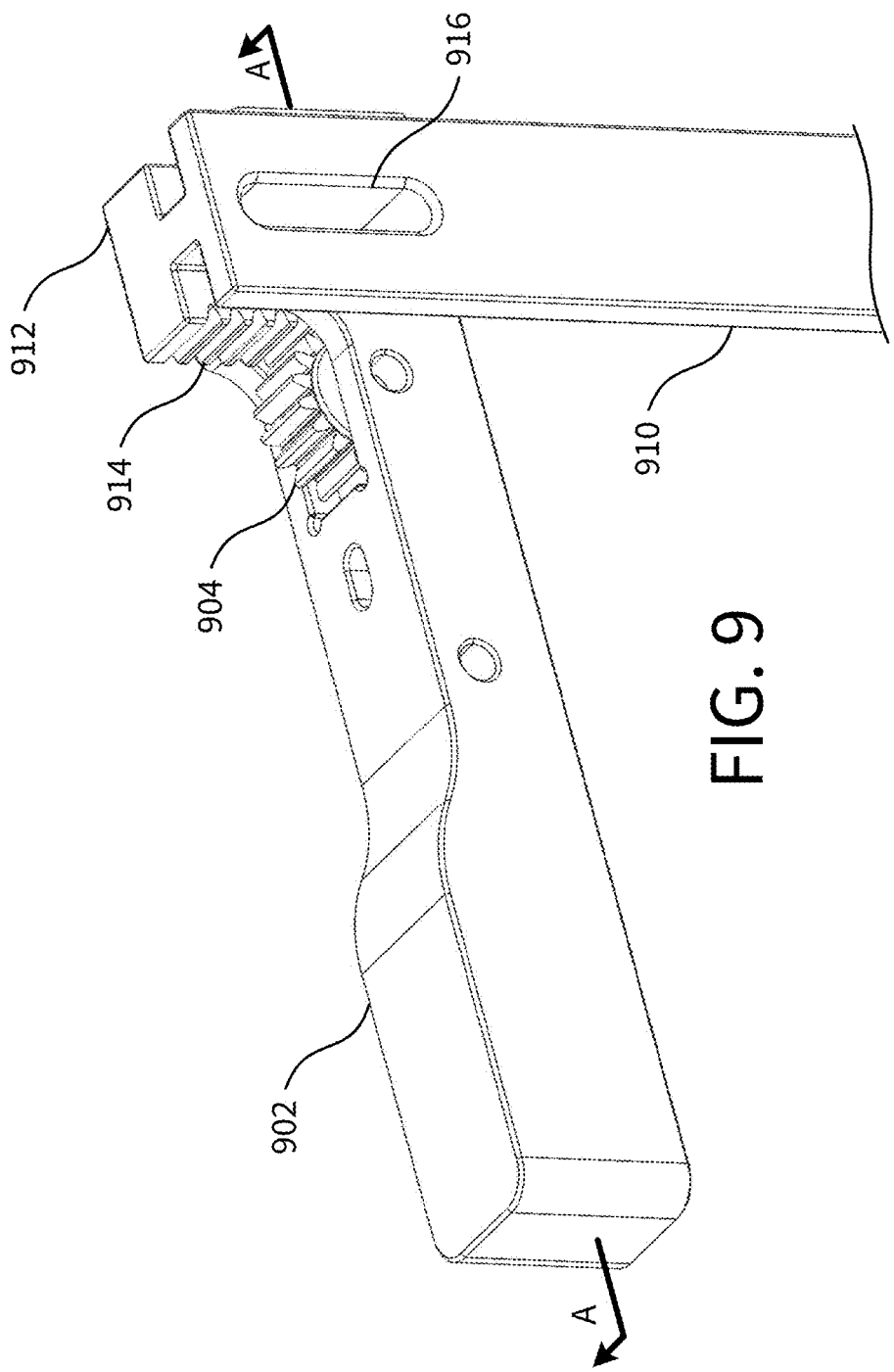
FIG. 9 illustrates a perspective view of a retractor arm and a retractor blade.
Figure 10:
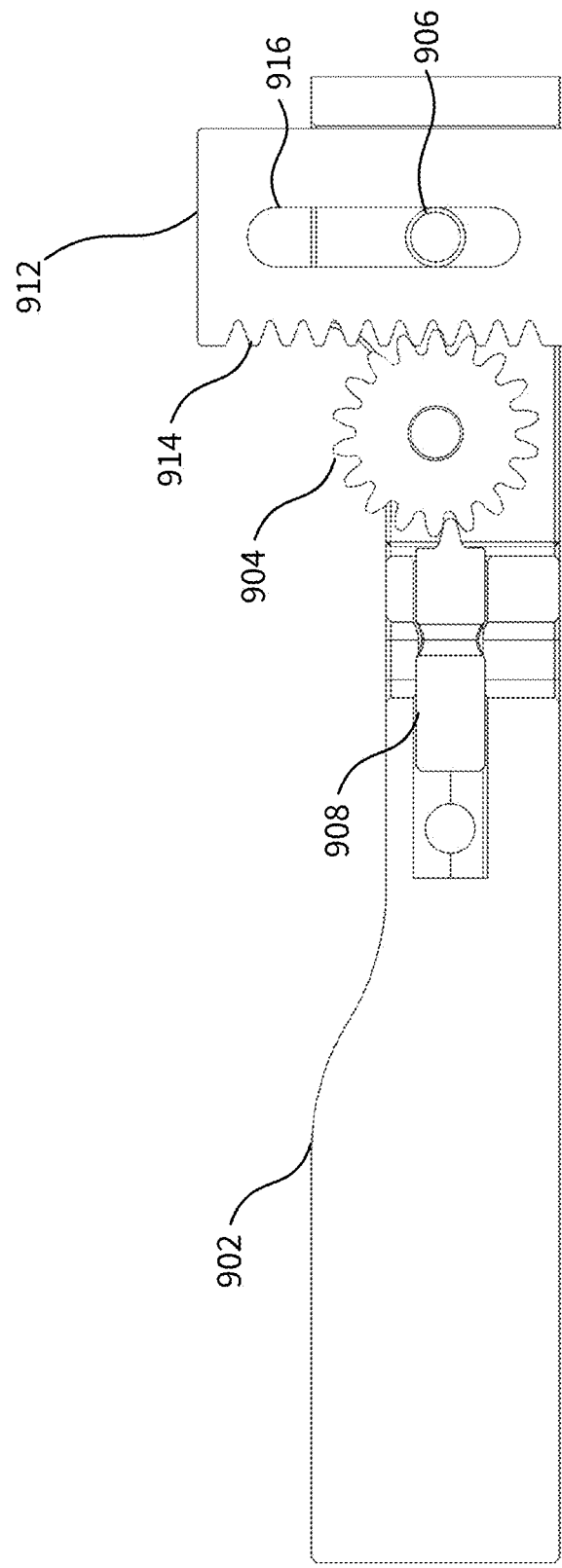
FIG. 10 illustrates a cross-sectional view of the retractor arm and blade of FIG. 9 along line A-A.

FIGS. 9 and 10 illustrate an example implementation of a retractor arm 902 and retractor blade 910 usable with examples described herein. In particular, FIG. 9 illustrates a perspective view of the retractor arm 902 and the retractor blade 910, and FIG. 10 illustrates a cross-sectional view of the retractor arm 902 and blade 910 along line A-A of FIG. 9. The retractor arm 902 can be coupled to a rack or retractor body in any number of suitable ways, including via connections described elsewhere herein. The illustrated implementation shows a coupling between the retractor blade 910 and the retractor arm 902 such that the retractor blade 910 is movable relative to the retractor arm 902. For example, the movement can result in the height of the retractor blade 910 being adjustable relative to the arm 902 (e.g., the relative amount of the retractor blade 910 above and below the retractor arm 902 can change). The movability can provide the user with the ability to adjust the height of the blade without needing to adjust the height of the arm 902.

As illustrated, the retractor blade 910 includes a proximal end 912. Disposed near the proximal end 912 is a blade height adjustment feature 914 that cooperates with an arm feature 904 of the arm. In the illustrated example, the blade height adjustment feature 914 is a rack that cooperates with the arm feature 904 in the form of a gear. A user can rotate the gear directly (e.g., with their thumb) or use a tool to rotate the gear (e.g., a screwdriver) to cause linear movement of the retractor blade 910. In other examples, the blade height adjustment feature 914 and the arm feature 904 can take any of a variety of forms, such as cooperating screw, ball-detent, or other mechanisms.

As further illustrated, the retractor blade 910 defines a track 916 in which a pin 906 of the arm 902 is disposed. The interaction between the pin 906 and the track 916 can constrain the relative movement of the arm 902 and the retractor blade 910. For example, the interaction can define a maximum amount of height adjustment of the retractor blade 910. The interaction can further constrain movement in other directions to provide a more stable connection between the blade 910 and the arm 902 (e.g., the pin-track relationship can resist movement of the retractor blade in a direction parallel to a length of the arm).

The retractor arm 902 can include a piston 908 or other feature that restricts movement of the arm feature 904. The piston 908 can resist unwanted movement of the blade 910 (e.g., the blade falling during use). In some examples, the piston 910 can be biased by a biaser (e.g., a spring) into interference with the arm feature 904. In some examples, the user can manually move the piston 908 to lock or unlock movement of the blade 910 with the arm feature 904.

Figure 11:
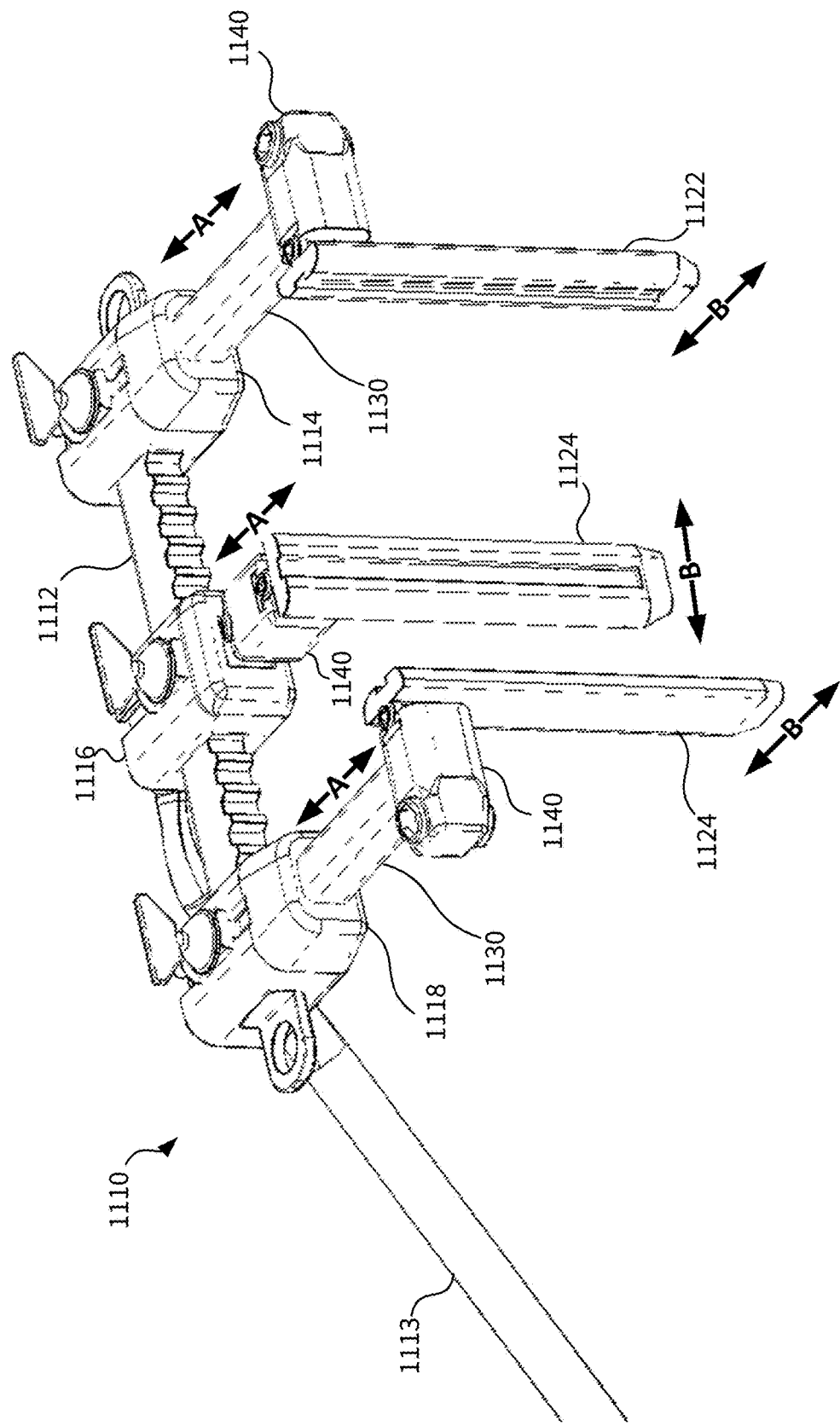
FIG. 11 illustrates a perspective view of an additional implementation of a retractor.
Figure 12:
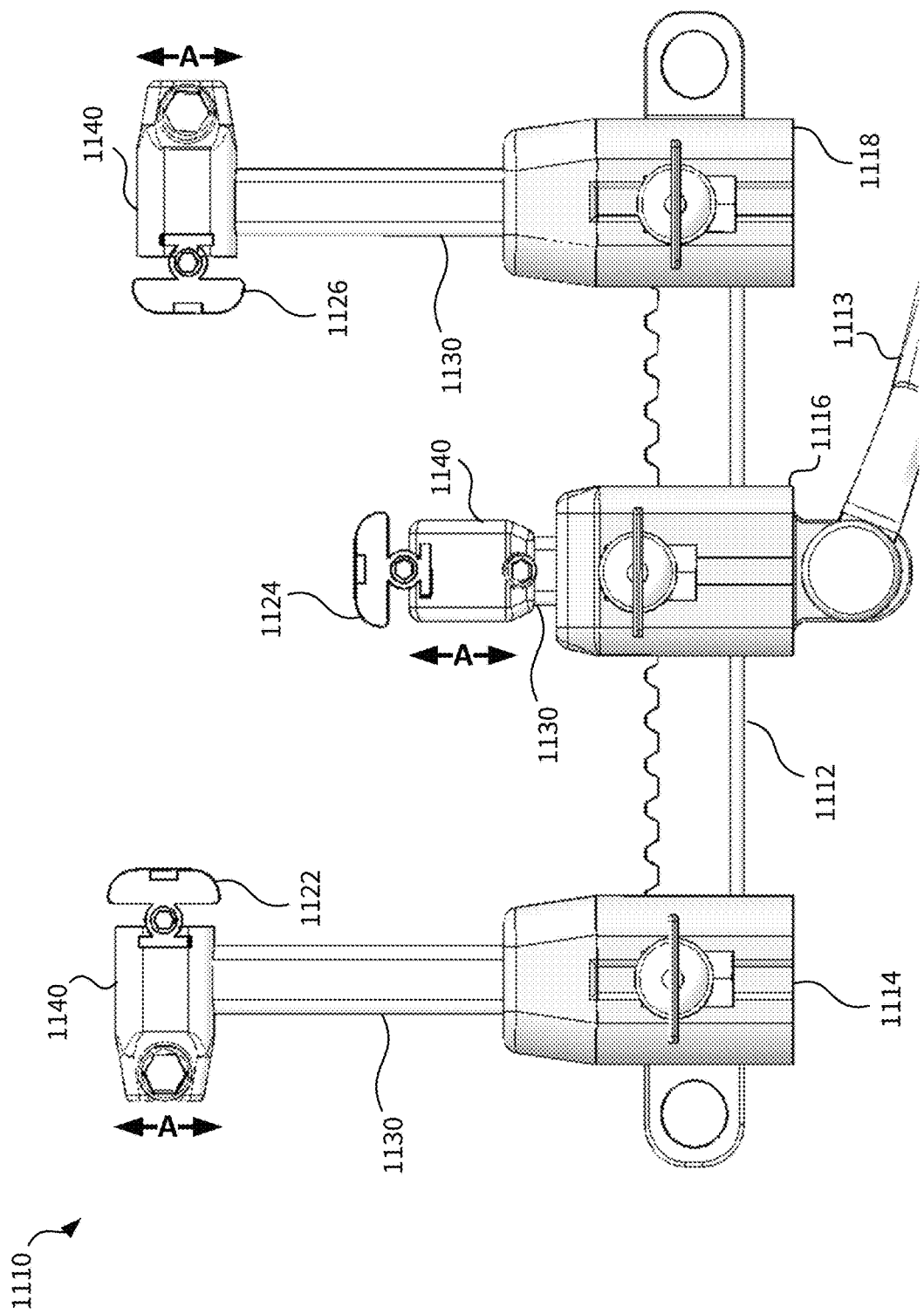
FIG. 12 illustrates a top view of the retractor of FIG. 11.

FIG. 11 illustrates a perspective view of an additional implementation of a retractor 1110 and FIG. 12 illustrates top view of the retractor 1110. The retractor 1110 can include one or more features of other retractors described herein, and the other retractors herein can include one or more features of the retractor 1110.

The retractor 1110 includes a rack 1112, a first arm 1114, a second arm 1116, and a third arm 1118. Respective first, second, and third retractor blades 1120, 1122, 1124 are coupled to distal ends of the first, second, and third arms 1114, 1116, 1118, respectively. The arms 1114, 1116, 1118 can be configured to be movable along a length of the rack 1112. The rack 1112 can be directly or indirectly coupled to a table or another structure via a link 1113. In the illustrated example, the link 1113 is coupled to the second arm 1116. The arms 1114, 1116, 1118 include movement sections 1130 that permit simultaneous or independent movement of the retractor blades 1120, 1122, 1124 closer or further away from the rack 1112 as shown by the arrows labeled with the letter A. In some examples, the retractor 1110 can be configured such that any combination of two or more of the first, second, and third arms 1114, 1116, 1118 can be moved simultaneously.

The movement provided by the movement sections 1130 can be achieved in any of a variety of ways. For example, the movement sections 1130 can provide telescoping movement, such as via at least one segment having an adjacent segment, in which a second segment extends along a first segment (either in full, or partially extended over). In other examples, a rack system or other mechanism can be used. Movement mechanisms can be additionally further defined to translate by way of, for example: along a helical rack by way of a pinion, long a ball-screw rack by way of a ball (bearing) nut, via hydraulically pressured telescoping arms, via pneumatically pressured telescoping arms, other mechanisms, or combinations thereof.

Further movement examples include the use of scissor-linkage extension, such as via at least one segment pair having an adjacent segment pair, in which translates in the direction of movement, Hydraulic or pneumatic pressure can be used for moving scissor-linkage arm pairs. In addition or instead, a helical screw mechanism can be used for movement of pair arms pairs.

As further illustrated, the retractor 1110 includes connections between the arms 1114, 1116, 1118 and the retractor blades 1120, 1122, 1124 with a wag mechanism 1140. The wag mechanism 1140 is a component configured to cause an end a retractor blade (e.g., the distal end or the proximal end) to wag side to side as shown by the arrows labeled with the letter B. The side to side movement can, for example, be in a plane parallel to the face of the retractor blade. The wag mechanism 1140 can cause greater side to side movement at the distal end of the blade than at the proximal end of the blade or vice versa. In an example, the wag mechanism 1140 is configured to permit the user to wag the blade independent of other movement of the blades. The wag mechanism 1140 can achieve the movement in any of a variety of ways. In an example, the wag mechanism 1140 can achieve movement using one or more of the following: spur gear (external gear), worm gear, spiral bevel gear, straight bevel gear, helical gear, screw gear (hypoid or hyperboloid gear), offset internal gear, rack-and-pinion configuration, other mechanisms, or combinations thereof.

In some examples, the retractor 1110 includes connections between the arms 1114, 1116, 1118 and the retractor blades 1120, 1122, 1124 with a blade height mechanism configured to adjust the height of the blade relative to the arm, such as is described in relation to FIGS. 8 and 9.

Patent application Ser. No. 15/386,999 filed Dec. 21, 2016, is herein incorporated by reference in its entirety for any and all purposes. This application describes a surgical retractor assembly that includes carriages movable within a track that hold retractor blade posts and allow the posts to move in multiple directions. One or more of the features of the carriages, blade posts, and track described therein can be applied to the carriages, blade posts, and track herein.

Patent application Ser. No. 15/926,064 filed Mar. 20, 2018, is herein incorporated by reference in its entirety for any and all purposes. This application describes a retractor that includes splayable arms. One or more of the features of this retractor can be applied to the arms described herein.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The detailed description should be read with reference to the drawings in which similar elements in different drawings are numbered the same. The drawings, which are not necessarily to scale, depict illustrative embodiments and are not intended to limit the scope of the disclosure.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A retraction system, comprising:
   a first retraction assembly, the first retraction assembly including:
      a first arm coupled to a rack;
      a second arm coupled to the rack;
      a first retractor blade coupled to the first arm;
      a second retractor blade coupled to the second arm;

a second retraction assembly, the second retraction assembly including:
- a carriage configured to engage a blade post having a blade coupled to a distal end and a handle coupled to a proximal end, the blade post adjustable relative to the carriage;
- a third retractor blade coupled to the blade post; and
- an adaptor having a first region configured to engage the rack and a second region configured to receive a portion of the carriage, wherein the second region permits the carriage to translate in a longitudinal direction of the rack while the first region remains engaged to the rack;
- wherein the carriage includes a projection, and wherein the adaptor includes a groove configured to engage the projection such that the projection is configured to translate within the groove of the adaptor, and wherein translation of the projection within the groove of the adaptor moves the third retractor blade in a cranial-caudal direction relative to a patient.

2. The retraction system of claim 1, wherein the adaptor is configured to translate relative to the rack.

3. The retraction system of claim 1, wherein the adaptor is fixed to the rack.

4. The retraction system of claim 1, wherein the adaptor includes a clamping mechanism configured to releasably secure the adaptor to the rack.

5. The retraction system of claim 1, wherein the adaptor includes an aperture; and wherein the rack extends through the aperture.

6. The retraction system of claim 1,
wherein the coupling between the first retractor blade and the first arm is such that height of the first retractor blade is adjustable relative to the first arm;
wherein the coupling between the second retractor blade and the second arm is such that height of the second retractor blade is adjustable relative to the second arm;
wherein the retractor system further includes a first wag mechanism configured to cause a first distal end of the first retractor blade to wag side to side;
wherein the retractor system further includes a second wag mechanism configured to cause a second distal end of the second retractor blade to wag side to side;
wherein the retractor further includes a first telescoping section configured to permit the first retractor blade to be moved closer to or further from the rack; and
wherein the retractor further includes a second telescoping section configured to permit the second retractor blade to be moved closer to or further from the rack.

7. The retraction system of claim 1, wherein the third retractor blade is configured to retract away from the first retractor blade and the second retractor blade to establish an operative corridor anterior to the psoas.

8. The retraction system of claim 1,
wherein the first retractor blade and the second retractor blade are configured to translate along a first plane;
wherein the third retractor blade is configured to retract along a second plane relative to the first plane; and
wherein retraction of the third retractor blade is configured to establish an operative corridor anterior to the psoas.

9. A retraction system for accessing the spine of a patient from an anterior-to-psoas approach, comprising:
- a first retraction assembly having a first retractor blade assembly coupled to a rack and a second retractor blade assembly coupled to the rack;
- a second retraction assembly having a third retractor blade assembly;
- an adaptor configured to couple the first retraction assembly to the second retraction assembly, the adaptor having a first region configured to engage the rack of the first retraction assembly and a second region configured to receive a portion of the second retraction assembly, and wherein the second region permits the second retraction assembly to translate in a longitudinal direction of the rack while the first region remains engaged to the rack; and
- a carriage configured to engage a blade post having a blade coupled to a distal end;
- wherein the carriage includes a projection, and wherein the adaptor includes a groove configured to engage the projection such that the projection is configured to translate within the groove of the adaptor, and wherein translation of the projection within the groove of the adaptor moves a third retractor assembly in a cranial-caudal direction relative to a patient; and
- wherein the first retraction assembly is coupled to the second retraction assembly such that adjustment of the first retractor blade assembly, the second retractor blade assembly or the third retractor blade assembly establishes an anterior-to-psoas operative corridor.

10. The retraction system of claim 9, wherein retraction of the second retraction assembly in an anterior direction relative to the first retraction assembly expands the operative corridor.

11. The retraction system of claim 9, wherein retraction of the third blade assembly in an anterior direction relative to the first retraction assembly expands the operative corridor.

12. The retraction system of claim 9, wherein retraction of the third retractor blade assembly in an anterior direction relative to the first retractor blade assembly, the second retractor blade assembly or both the first and second retractor blade assemblies expands the operative corridor.

13. The retraction system of claim 9, wherein the adaptor is configured to translate relative to the first retraction assembly.

14. The retraction system of claim 9, wherein the adaptor is releasably adjustable relative to the first retraction assembly.

* * * * *